United States Patent
Kalbfleisch et al.

(10) Patent No.: US 7,306,790 B2
(45) Date of Patent: Dec. 11, 2007

(54) TWO-PHASE HAIR GEL

(75) Inventors: Axel Kalbfleisch, Darmstadt (DE);
Thomas Krause, Darmstadt (DE);
Gerhard Sendelbach, Darmstadt (DE);
Angelika Beyer, Waldaschaff (DE);
Sabine Baecker, Ruesselsheim (DE);
Matthias Pfaffernoschke, Oberkirch (CH)

(73) Assignee: Wella AG, Darmstadt (DE)

( * ) Notice: Subject to any disclaimer, the term of this patent is extended or adjusted under 35 U.S.C. 154(b) by 0 days.

(21) Appl. No.: 10/479,327

(22) PCT Filed: May 5, 2002

(86) PCT No.: PCT/EP02/04807

§ 371 (c)(1),
(2), (4) Date: Apr. 1, 2004

(87) PCT Pub. No.: WO02/098371

PCT Pub. Date: Dec. 12, 2002

(65) Prior Publication Data

US 2004/0151683 A1    Aug. 5, 2004

(30) Foreign Application Priority Data

Jun. 2, 2001  (DE) ................. 101 27 104

(51) Int. Cl.
*A61Q 5/06* (2006.01)

(52) U.S. Cl. ............. 424/70.2; 424/45; 424/70.11
(58) Field of Classification Search ........... 424/70.1
See application file for complete search history.

(56) References Cited

U.S. PATENT DOCUMENTS

| | | | | |
|---|---|---|---|---|
| 5,726,138 | A  * | 3/1998 | Tsaur et al. ............... | 510/158 |
| 6,264,929 | B1 * | 7/2001 | Karlen et al. ............. | 424/70.1 |
| 6,547,503 | B1 * | 4/2003 | Bohm et al. ............... | 413/4 |
| 6,623,727 | B2 * | 9/2003 | Birkel et al. .............. | 424/70.1 |
| 2001/0006653 | A1 * | 7/2001 | Roulier et al. ............ | 424/400 |

FOREIGN PATENT DOCUMENTS

| | | |
|---|---|---|
| DE | 22 20 662 A | 11/1972 |
| EP | 0 923 931 | 6/1999 |
| WO | 96 40815 | 12/1996 |
| WO | 98 08601 A | 3/1998 |
| WO | 99 51716 A | 10/1999 |
| WO | WO 99/51716 | * 10/1999 |

* cited by examiner

*Primary Examiner*—Jyothsna Venkat
(74) *Attorney, Agent, or Firm*—Michael J. Striker

(57) ABSTRACT

The object of the invention is a hair-treatment agent in the form of a two-phase gel, containing comminuted particles of a firm and shape-retaining gel based on a carrageenan-containing aqueous base in a fluid polyol matrix. The gel is a clear product with properties of a hair wax or hair cream and it can be dispensed, sprayed or foamed from a suitable container by means of a propellant.

12 Claims, No Drawings

TWO-PHASE HAIR GEL

The object of the invention is a hair-treatment agent in the form of a two-phase gel containing comminuted particles of a firm, shape-retaining gel in a fluid matrix.

Hair-treatment agents in the form of thickened preparations, for example gels, hair creams or hair waxes, are used to confer firmness, hold, stylability or luster to human hair or to stabilize a finished hairdo. Such products have a highly viscous yet fluid to semifirm or creamy, uniform, homogeneous consistency. Besides the aforesaid primary product performance characteristics, haptics and consistency are of essential importance for the product quality of cosmetic hair preparations. In particular, of special interest are clear products and those with novel product consistency and with novel, unusual properties. Such a property is, for example, a special sensory, particularly tactile effect appearing, for example, during the use of the cosmetic agent, namely special haptics. These novel, unusual properties should, of course, not impair the primary product characteristics and in the ideal case should even potentiate them. Moreover, easy, problem-free application and good distribution in the hair, in particular, should be ensured.

The purpose of the invention was to provide cosmetic agents with novel, unusual haptic properties. If possible, these agents were to be clear and exhibit the typical properties of a hair wax or hair cream, for example the ability to confer stylability, hold, luster etc. Moreover, these agents were to have good application properties, be readily rubbed into the hair and distributed on it. In particular, the purpose was to provide a hair gel with firm particles readily distributed in the hair.

EP 0 923 931 discloses firm cosmetic agents containing at least 2% of kappa-carrageenan in combination with certain hydrocolloids of natural origin and, in essence, used as personal-care sticks (lipsticks). These agents require relatively high amounts of carrageenan to attain the required firmness. Such agents are not suitable for hair treatment, because as a result of the high carrageenan content (more than 2%), they can form unsightly, visible residues on the hair. If the carrageenan content is reduced, the product no longer shows sufficient firmness.

We have now found that the above objective can be achieved by use of a hair-treatment agent in the form of a two-phase gel, wherein one phase consists of particles of a firm, shape-retaining gel, and the other phase acts as a fluid matrix for the firm particles, and wherein the fluid phase contains at least one polyhydric alcohol or at least one liquid polyether derived from a polyhydric alcohol. The amount of the firm gel phase is preferably from 30 to 95 wt. % of the total preparation, an amount from 50 to 85 wt. % being particularly preferred, and correspondingly the amount of the fluid matrix preferably is from 5 to 70 wt. % and particularly from 15 to 50 wt. %.

The liquids contained in the fluid phase are preferably selected from among the alkylene glycols, glycerol and liquid polyalkylene glycols, the alkylene groups preferably containing from 2 to 5 carbon atoms. Suitable are, for example, ethylene glycol, the propylene glycols, particularly 1,2-propylene glycol, butylene glycol, the pentanediols, the polyethylene glycols that are liquid at 25° C., polypropylene glycols, polyethylene glycol $C_1$-$C_4$-alkyl ethers, polypropylene glycol $C_1$-$C_4$-alkyl ethers, ethylene glycol-propylene glycol copolymers or polyoxyethylene-polyoxypropylene $C_1$-$C_4$-alkyl ethers. Suitable polyethylene glycols have a molecular weight between 150 and 700, and preferably between 170 and 300 g/mol. Suitable low-molecular-weight polyethylene glycols are those having the formula $H(OCH_2CH_2)_nOH$ with n=4 to 14, preferably with n=4 to 8. Suitable polyethylene glycols have the INCI designation PEG-4 (n=4), PEG-6 (n=6), PEG-7 (n=7), PEG-8 (n=8), PEG-9 (n=9), PEG-10 (n=10), PEG-12 (n=12) and PEG-14 (n=14). A suitable commercial product is, for example, Polyglycol 200 with a molecular weight from 190 to 210, supplied by Clariant. Particularly preferred are glycerol, PEG-4 and PEG-6.

The firm phase of the product of the invention consists of a firm, shape-retaining gel. For purposes of the invention, firm and shape-retaining are, in particular, compositions showing a resistance to compression under standard conditions (20° C., 65% rel. humidity) amounting to at least 0.15 N, preferably to 0.30 to 2.0 N, and particularly to 0.40 to 1.5 N, as measured by penetration of the firm gel with a cylindrical plunger having a diameter of 8 mm, the penetration being carried out at a rate of 0.5 mm/sec to a compression depth of 1 mm, after which the plunger is withdrawn at a rate of 0.5 mm/sec. The shape of the gel is retained at least at room temperature (20° C.) or below, preferably at a temperature up to 30° C. and particularly at a temperature up to 35° C.

The preferred gel-forming agent for the firm gel phase is carrageenan. Normally, an amount of carrageenan of at least about 3 wt. % in water is needed to obtain a firm and shape-retaining gel. To prevent the formation of a visible residue on the hair, however, it is advisable to reduce the amount of carrageenan. The required gel firmness can in this case be attained by adding for the preparation of the firm gel phase at least one hair-firming polymer and/or at least 15 wt. % of at least one monohydric or polyhydric alcohol and/or at least one salt containing calcium ions or potassium ions. Such compositions show sufficient firmness of the firm gel phase even with low amounts of carrageenan (for example below 2 wt. %). In this manner, it is possible to use said compositions for hair treatment, particularly when for hair firming purposes hair-firming polymers are added as hair-styling agents, because the problem of undesirable residue formation has been solved.

In a preferred embodiment of the invention, the firm gel phase is in the form of a firm and shape-retaining gel containing a combination of (A) carrageenan and (B) at least one hair-firming polymer in a water-containing base. Carrageenan and the hair-firming polymer are present in amounts such that the gel is firm and shape-retaining at room temperature (20° C.).

Carrageenan

A suitable gel-former is carrageenan, particularly kappa- or iota-carrageenan. Particularly preferred is kappa-carrageenan or a carrageenan mixture containing kappa-carrageenan. Particularly well suited is, for example, a carrageenan of medium molecular weight such as Sea Kem® CM 611 supplied by FMC Corporation. The gel former is used in an amount such that the firm phase of the agent is a firm, shape-retaining gel at room temperature (20° C.). Suitable is an amount of, for example, 0.5 to 5 wt. %, preferably from 1 to less than 2.5 wt. % and particularly from 1.3 to 2 wt. % or less. In some cases, firmness can be attained only after some time has elapsed, for example in the course of two to three days. Gel firming can be accelerated by first dissolving the gel former in water optionally by heating to about 80° C., and then cooling rapidly to at least 50 to 55° C. or lower by applying additional external cooling.

Calcium Ions and Potassium Ions

The calcium ions and/or potassium ions are used in the form of water-soluble salts, for example halides, sulfates etc., among which the chlorides are preferred. The salts are preferably used in an amount from 0.2 to 1 wt. % and particularly from 0.4 to 0.8 wt. %. Potassium ions are preferred, because they afford clearer, non-turbid gels.

Hair-Firming Polymers

We have found that firm gels of pure carrageenan exert a certain hair-firming action even without additional hair-firming polymers. For sufficient hair-firming, however, relatively high amounts of carrageenan are needed with the undesirable side effect of visible residue formation on the hair. Reduction in the amount of carrageenan causes a loss in adequate hair firming as well as a loss in the firmness and shape retention of the gel. The agent of the invention therefore contains at least one additional, synthetic or natural hair-firming polymer. Said polymer can be contained in the fluid matrix or preferably in the firm gel phase.

The additional hair-firming polymer is preferably present in an amount from 0.1 to 30 wt. % and particularly from 0.5 to 15 wt. %. The hair-firming polymer can be nonionic, anionic, zwitterionic or amphoteric. Particularly preferred are polymers containing no cationic groups, namely anionic, nonionic and amphoteric polymers. By synthetic polymers are meant polymers of purely synthetic, non-natural origin, particularly those obtained by free-radical polymerization from ethylenically unsaturated monomers or by polycondensation. Particularly preferred are polymers having sufficient solubility or dispersibility in water, alcohol or water/alcohol mixtures, so that they are present in the water-based agent of the invention in dissolved or uniformly dispersed form. According to the invention, by hair-firming polymers are meant polymers which when used in an amount from 0.01 to 5% in aqueous, alcoholic or aqueous-alcoholic solution are capable of depositing a polymer film on the hair thus firming the hair.

It is particularly preferred to use in the gel of the invention film-forming, hair-firming, nonionic, anionic or amphoteric polymers. Suitable nonionic polymers are the homopolymers and copolymers derived from at least one of the following monomers: vinylpyrrolidone, vinylcaprolactam, a vinyl ester such as, for example, vinyl acetate, vinyl alcohol, acrylamide, methacrylamide, alkylacrylamide, dialkylacrylamide, alkylmethacrylamide, dialkylmethacrylamide, alkyl acrylate, alkyl methacrylate, propylene glycol or ethylene glycol, the alkyl groups of these monomers preferably being $C_1$- to $C_7$-alkyl groups and particularly $C_1$- to $C_3$-alkyl groups. Suitable are, for example, homopolymers of vinylcaprolactam, vinylpyrrolidone or N-vinylformamide. Other suitable synthetic film-forming, nonionic, hair-firming polymers are, for example, the copolymers of vinylpyrrolidone and vinyl acetate, the terpolymers of vinylpyrrolidone, vinyl acetate and vinyl propionate, the polyacrylamides marketed, for example, under the commercial name of Akypomine® P 191 by CHEM-Y, Emmerich, or under the name of Sepigel® 305 by Seppic; furthermore polyvinyl alcohols marketed, for example, by DuPont under the commercial name Elvanol® or by Air Products under the name of Vinol® 523/540, as well as the polyethylene glycol-polypropylene glycol copolymers marketed, for example, by Union Carbide under the commercial name of Ucon®. Particularly preferred are polyvinylpyrrolidone, polyvinylcaprolactam and the copolymers thereof with at least one additional nonionic monomer, particularly polyvinylpyrrolidone-vinyl acetate copolymers.

Suitable anionic hair-firming polymers are the synthetic homopolymers or copolymers of acid groups-containing monomers optionally copolymerized with comonomers devoid of acid groups. The acid groups are preferably selected from among —COOH, —SO$_3$H, —OSO$_3$H, —OPO$_2$H and —O—PO$_3$H$_2$, among which the carboxylic acid groups are preferred. The acid groups can be present in non-neutralized or partly or completely neutralized form. They are preferably present to an extent of 50 to 100% in anionic or neutralized form. Suitable neutralizing agents are organic or inorganic bases employed for cosmetic purposes. Examples of bases are the aminoalcohols, for example aminomethylpropanol (AMP), triethanolamine, monoethanolamine or tetrahydroxypropylethylenediamine and ammonia, NaOH and others. Suitable monomers are unsaturated, free radical-polymerizable compounds bearing at least one acid group, particularly carboxyvinyl monomers. Suitable acid groups-containing monomers are, for example, acrylic acid, methacrylic acid, crotonic acid, maleic acid or maleic anhydride or the monoesters thereof.

Suitable comonomers devoid of acid group substituents are, for example, acrylamide, methacrylamide, alkylacrylamide and dialkylacrylamide, alkyl methacrylamide and dialkyl methacrylamide, alkyl acrylate, alkyl methacrylate, vinylcaprolactone, vinylpyrrolidone, vinyl esters, vinyl alcohol, propylene glycol or ethylene glycol, amino-substituted vinyl monomers, for example dialkylaminoalkyl acrylate, dialkylaminoalkyl methacrylate, monoalkylaminoalkyl acrylate and monoalkylaminoalkyl methacrylate, the alkyl groups of these monomers preferably being $C_1$- to $C_7$-alkyl groups and particularly $C_1$- to $C_3$-alkyl groups.

Suitable polymers with acid groups are, in particular, the copolymers of acrylic acid or methacrylic acid with monomers selected from among the acrylate or methacrylate esters, acrylamides, methacrylamides and vinylpyrrolidone, the homopolymers of crotonic acid and the copolymers of crotonic acid with monomers selected from among the vinyl esters, acrylate and methacrylate esters, acrylamides and methacrylamides. A suitable natural polymer is, for example, shellac.

Preferred polymers with acid groups are the crosslinked or noncrosslinked vinyl acetate-crotonic acid copolymers. Also preferred are the partly esterified copolymers of vinyl methyl ether and maleic anhydride. Other preferred anionic polymers are, for example, the terpolymers of acrylic acid, alkyl acrylate and N-alkylacrylamide, particularly the acrylic acid-ethyl acrylate-N-tert.butylacrylamide terpolymers or the terpolymers of vinyl acetate, crotonate and vinyl neodecanoate, particularly vinyl acetate-crotonate-vinyl neodecanoate copolymers, as well as the copolymers of acrylic or methacrylic acid and alkyl acrylate esters or methacrylate esters, the alkyl groups preferably containing from 1 to 7 carbon atoms.

Suitable amphoteric hair-firming polymers are polymers which besides acid or anionic groups contain as additional functional groups basic or cationic groups, particularly primary, secondary, tertiary or quaternary amino groups. Examples of such polymers are the copolymers derived from alkylacrylamide (particularly octylacrylamide), an alkylaminoalkyl methacrylate (particularly tert.butylaminoethyl methacrylate) and two or more monomers consisting of acrylic acid, methacrylic acid or an ester thereof, for example the polymers available under the commercial name Amphomer® or Amphomer® LV-71, supplied by NATIONAL STARCH, USA. Other examples of copolymers with acid groups suitable as component (B) are the copolymers of acrylic acid, methyl acrylate and methacrylamidopropyltrimethylammonium chloride (INCI designation: Polyquaternium-47), such as those marketed by Calgon under the commercial name Merquat® 2001, the copolymers of acrylamidopropyltrimethyl-ammonium chloride and acrylates, for example such as those obtainable from Stockhausen under the commercial name W 37194, or the copolymers of acrylamide, acrylamidopropyltrimethylammonium chloride, 2-amidopropylacrylamidosulfonate and dimethylaminopropylamine (INCI designation: Polyquaternium-43), such as those marketed, for example, by Société Francaise Hoechst under the commercial name Bozequat® 4000. Also suitable are the polymers of betaine groups-bearing monomers, for example the copolymers of methacryloyl ethylbetaine and two or more monomers of acrylic acid or a simple ester thereof, known under the INCI designation Methacryloyl Ethyl Betaine/Acrylates Copolymer.

Aqueous Base

The firm gel according to the invention is preferably formulated in an aqueous base. By this is meant either a purely aqueous medium or an aqueous-alcoholic medium with preferably up to 40 wt. % of alcohol. Suitable alcohols are, in particular, the lower monohydric or polyhydric alcohols with 1 to 5 carbon atoms commonly used for cosmetic purposes, for example ethanol, isopropanol, ethylene glycol, glycerol and the propylene glycols, particularly 1,2-propylene glycol. Typical water contents are from 55 to 95 wt. %, and preferably from 65 to 80 wt. %, and typical alcohol contents are from 0 to 30 wt. % and preferably from 1 to 25 wt. %. Alcohol contents above 40 wt. % may cause the carrageenan to precipitate.

Particularly advantageous is the use of at least 15 wt. % of alcohol, because it is thereby possible to attain sufficient gel firmness and shape retention even with an amount of carrageenan that is below the otherwise required minimum of 2.5 to 3 wt. %, particularly an amount below 2 wt. %. Moreover, by using at least 15 wt. % of alcohol, an additional preservative is not absolutely necessary.

A particular advantage of the gel according to the invention is that its viscosity remains stable over a wide range of pH from 1 to 14. Particularly preferred is the pH range between 2.5 and 8.

Preservative

Because the carrageenan used for the gel according to the invention is a saccharide-based polymer of natural origin, the agent of the invention requires special attention to be directed to its preservation so as to ensure its prolonged stability. Particularly well suited preservatives are the parabens, for example methyl paraben. At ethanol contents of about 15 wt. % and higher, an additional preservative is not absolutely necessary.

Sugar

For improved clarity and transparency of the agent of the invention, the formulation should advantageously also contain at least one sugar. Said sugar is preferably contained in the firm gel phase. Suitable sugars are, in particular, monosaccharides and disaccharides, for example glucose, galactose, fructose, maltose, lactose or sucrose. Typically, they are used in an amount from 0.01 to 5 wt. % and preferably from 0.05 to 1 wt. %. Preferred are ready-made mixtures of carrageenan and sugar, for example the raw material Seakem CM 611 which is a mixture of carrageenan and dextrose.

Additives for Improved Spreading and Distribution

To improve spreadability in the hands and distribution on the hair or to further optimize the consistency, the agent according to the invention preferably contains other thickeners or gel formers. These can be contained in the liquid matrix or preferably in the firm gel phase. Suitable to this end are, for example, carboxyvinyl polymers, particularly polyacrylates, for example the various Carbopol brands, furthermore polyglycols, cellulose derivatives, particularly hydroxyalkylcelluloses, as well as inorganic thickeners, for example the natural or synthetic bentonites. Typically, the additional gel formers and thickeners are used at a concentration from about 0.2 to 10.0 wt. % and preferably from 1 to 5 wt. %.

Suitable substances that facilitate the spreading of the gel or its distribution on hair are xanthan gum and cellulose derivatives such as those described in EP 0 923 931. Said substances are hydrocolloids that are readily soluble in hot water, particular examples being carboxymethylcellulose and hydroxyethylcellulose.

Surprisingly, we have now found that particularly good spreading and distribution of carrageenan-based firm gels can be attained by use of amphiphilic associative thickeners. Suitable amphiphilic associative thickeners are nonionic polymers containing both hydrophilic and hydrophobic groups. Associative thickeners are water-soluble polymers containing surfactant-like hydrophobic parts which in a hydrophilic, particularly aqueous medium are capable of undergoing association, namely interaction, with themselves as well as with other hydrophobic substances. The resulting associative network causes the medium to thicken or to gel. Typically, associative thickeners are prepared by polymerization of polyethylene oxide pre-polymers and at least difunctional polycondensable substances, for example isocyanates, whereby monohydric alcohols or diols with large aryl, alkyl or arylalkyl groups are incorporated to provide the hydrophobic modification. Preferred associative thickeners are therefore hydrophobically modified polyalkylene glycols. The hydrophilic part of such thickeners consists of polyoxyalkylene units, preferably polyoxyethylene units but also polyoxypropylene ones or a mixture thereof. The hydrophobic part preferably consists of hydrocarbon groups, for example long-chain alkyl groups, alkylaryl groups or arylalkyl groups.

Particularly preferred associative thickeners are the hydrophobically modified aminoplast-polyether copolymers. For their structure and preparation, the reader is referred to WO 96/40815. In WO 96/40815 are described water-dispersible or water-soluble copolymers that are reaction products of acid-catalyzed polycondensation of at least difunctional aminoplast monomers and at least difunctional alkylene polyethers as well as monofunctional compounds with hydrophobic groups. Suitable aminoplasts are shown in FIG. 1 of WO 96/40815. Particularly preferred are the glycoluril derivatives of formula X of WO 96/40815. Suitable alkylene polyethers can be seen in FIG. 2 of WO 96/40815. Preferred alkylene polyethers are the polyethylene oxide diols. They can have an ethoxylation degree from 20 to 500, preferably from 50 to 350 and particularly from 100 to 250. Suitable monofunctional compounds with hydrophobic groups are those of Formula XIV of WO 96/40815.

Suitable associative thickeners according to the invention are selected from among the polymers of general formula (I)

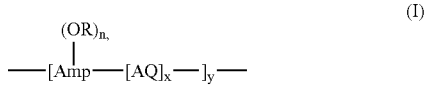

wherein Amp denotes an aminoplast monomer or the residue of an aminoplast oligomer or aminoplast polymer, AO stands for an alkylene oxide group, R for hydrogen, $C_1$-$C_4$-alkyl or $C_1$-$C_4$-acyl, x and y denote numerals greater than 1 and n is a positive number indicating the number of free bonds of Amp. Particularly preferred are the reaction products of the acid-catalyzed polycondensation of (a) a glycoluril of general formula (II)

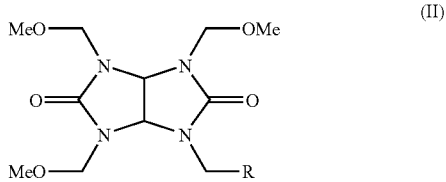

wherein R stands for H or preferably for OMe, with b) a polyethylene oxide diol having a degree of ethoxylation from 20 to 500, preferably from 50 to 350 and particularly from 100 to 250, and (c) an optionally ethoxylated hydrophobic alcohol, alkylphenol, thiol, carboxamide, carbamate or a hydrophobic carboxylic acid such as those described on pages 17 to 19 of WO 96/40815. A particularly preferred glycoluril is 1,3,4,6-tetramethoxymethyl glycoluril.

Suitable associative thickeners are those with an INCI designation Polyether-1, PEG-180/Octoxynol-40/TMMG Copolymer and PEG-180/Laureth-50/TMMG Copolymer, marketed by Süd Chemie under the commercial names Pure-Thix® HH, L, M or TX.

Optional Additives

The agent of the invention can additionally contain in the firm gel phase and/or fluid matrix additives commonly used for hair-treatment agents, for example wetting agents or emulsifiers, in an amount from 0.1 to 15 wt. %; moisturizing agents; perfume oils in an amount from 0.1 to 0.5 wt. %; bactericidal and fungicidal agents, for example 2,4,4-trichloro-2-hydroxydiphenyl ether or methylchloroisothiazole ion [sic] in an amount from 0.01 to 1.0 wt. %; buffers, for example sodium citrate or sodium phosphate, in an amount from 0.1 to 1.0 wt. %; coloring agents, for example sodium fluorescein, in an amount from about 0.1 to 1.0 wt. %; hair-care agents, for example vegetable and herb extracts, protein hydrolyzates and silk hydrolyzates, lanoline derivatives, in an amount from 0.1 to 5 wt. %; physiologically compatible silicone derivatives, for example volatile or nonvolatile silicone oils or high-molecular-weight siloxane polymers, in an amount from 0.05 to 20 wt. %; light-protective agents, antioxidants, free-radical scavengers, antidandruff agents, in an amount from about 0.01 to 2 wt. %; luster-imparting agents, vitamins, softeners, combability improvers and regreasing agents.

Method of Preparation

The agent of the invention can be prepared by first preparing a firm, shape-retaining gel, comminuting said firm gel mechanically into individual particles and then adding to said particles a liquid containing at least one polyhydric alcohol or at least one liquid polyether derived from a polyhydric alcohol.

The firm gel can be prepared by first dissolving the carrageenan and optionally other active and auxiliary hair-cosmetic agents in an aqueous solvent, the amount of the gel former and the kind and amounts of the other active and auxiliary hair-cosmetic agents being selected so that a shape-retaining, firm gel can form. If the gel former or the additives are not completely soluble at room temperature, they can be made to dissolve by heating the mixture to, for example, about 40-80° C. The solution is then allowed to stand until the gel firms up. Advantageously, this process is accelerated by applying additional external cooling to at least 50-55° C. or lower. The firm gel is then comminuted into particles by means of an appropriate cutting or stamping tool. The particle size (average diameter) is preferably from 0.1 to 10 mm, particularly from 0.5 to 5 mm and more preferably from 1 to 5 mm. The liquid matrix is added to these particles, and the mixture is stirred until the firm gel particles are uniformly distributed in the liquid matrix.

Embodiment of the Invention with a Propellant Content

In a special embodiment, the agent according to the invention contains additionally at least one propellant. Hence, an object of the invention is also a hair-treatment agent consisting of (a) a pressure-resistant container containing (b) a propellant-containing hair-treatment agent in the form of the above-described two-phase gel with comminuted particles of a firm and shape-retaining gel in a fluid matrix and (c) a device for spraying or foaming the hair-treatment agent. In other words, this agent is a three-phase agent. It contains a first (firm) phase consisting of particles of a firm and shape-retaining gel. A second (liquid) phase serves as matrix for the firm gel particles, and the propellant forms a third (gaseous) phase. The weight ratio of the active agent composition consisting of gel particles and fluid matrix to the amount of propellant is preferably from 60 to 80 wt. %, and more preferably from 65 to 70 wt. %, of active agent composition to 20 to 40 wt. %, and preferably from 30 to 35 wt. %, of propellant.

Suitable propellants are, for example, the lower alkanes, for example propane, n-butane, isobutane or mixtures thereof, as well as dimethyl ether or fluorocarbons such as F-152a (1,1-difluoroethane) or F-134 (tetrafluoroethane) and also propellants that are gaseous at the pressures involved, for example $N_2$, $N_2O$ and $CO_2$, as well as mixtures of the aforesaid propellants. Particularly preferred is dimethyl ether. It is especially advantageous to add to the primary propellant a small amount, for example 1 to 10 wt. %, of pentane.

The propellant-containing hair-treatment product has as an additional component a device for spraying or foaming the composition. A commercial spraying head or foaming head can be used for this purpose. The propellant-containing composition is introduced into a pressure-resistant container. The container material for this purpose can be a common metallic material such as aluminum or tinplate, or else glass or a pressure-resistant plastic material such as polyethylene, polypropylene or polyethylene terephthalate. Particularly preferred are clear, transparent materials, especially glass and transparent plastics. The preparation involves first preparing the two-phase composition of firm gel particles and fluid matrix as described hereinabove and then filling the pressure-resistant container with this mixture and the propellant.

The propellant-containing embodiment of the invention exhibits special advantages in that it markedly improves the spreadability of the composition in the hands and its distribution on the hair. Moreover, a special sensory, cooling effect is achieved.

The following examples are intended to illustrate the subject matter of the invention more closely. The polymer quantities given in the examples always refer to the solids content.

EXAMPLES

Example 1

| | |
|---|---|
| 1.6 g | of Sea Kem ® CM 611 (carrageenan and dextrose, FMC Corp.) |
| 2.5 g | of Luviset ® CA 66 (vinyl acetate-crotonic acid copolymer, BASF) |
| 0.27 g | of aminomethylpropanol (95%) |
| 2.5 g | of Pure Thix ® 1442 (Polyether-1, Sud Chemie, United Catalysts) |
| 20 g | of ethanol |
| to 100 g | water |

To prepare the gel phase, the above constituents were heated to about 70° C. to dissolve them in the solvent. The mixture was then cooled to room temperature by allowing it to stand, thus causing the gel to firm up. By means of a spatula, the firm gel was comminuted into small irregular pieces having an average diameter from 2 to 4 mm. 28 wt. % of glycerol was then added to 72 wt. % of the comminuted firm gel particles, and the mixture was carefully stirred.

Example 2

Comminuted firm gel particles were prepared as in Example 1. 33 wt. % of PEG-4 (Polyglycol 200) was added to 67 wt. % of firm gel particles, and the mixture was carefully stirred.

Example 3

| | |
|---|---|
| 1.5 g | of Sea Kem ® CM 611 (carrageenan and dextrose, FMC Corp.) |
| 30 g | of ethanol |
| to 100 g | water |

To prepare the gel phase, the above constituents were heated to about 70° C. to dissolve them in the solvent. The mixture was then cooled to room temperature by allowing it to stand, thus causing the gel to firm up. By means of a spatula, the firm gel was comminuted into small irregular pieces having an average diameter from 2 to 4 mm. 33 wt. % of glycerol was then added to 67 wt. % of the comminuted firm gel particles, and the mixture was carefully stirred.

Example 4

Comminuted firm gel particles were prepared as in Example 3. 33 wt. % of PEG-4 (Polyglycol 200) was added to 67 wt. % of firm gel particles, and the mixture was carefully stirred.

Example 5

65 wt. % of the composition of Example 1 and 35 wt. % of dimethyl ether were placed into an aerosol can.

Example 6

70 wt. % of the composition of Example 2 and 30 wt. % of dimethyl ether were placed into an aerosol can.

Example 7

70 wt. % of the composition of Example 3 and 30 wt. % of dimethyl ether were placed into an aerosol can.

In all examples, the two-phase consistency of the firm gel particles and liquid matrix was retained even after a one-week storage period at 40° C.

The preparations were readily distributed on the hair. They conferred stylability, flexible hold and stability to the hairdo and gave the hair a moist and lustrous appearance.

The invention claimed is:

1. A hair-treatment agent in the form of a two-phase gel, said two-phase gel consisting of a firm particle phase and a fluid phase;
    wherein said firm particle phase consists of firm particles and said fluid phase consists of a fluid matrix for said firm particles, said firm particles having an average particle diameter of 1 mm to 10 mm and consisting of a firm and shape-retaining gel;
    wherein said firm and shape-retaining gel contains from 1 wt. % to below 2 wt. % of carrageenan, from 0.5 to 15 wt. % of at least one hair-firming polymer, and at least one substance capable of increasing firmness of the firm particles in a water-containing base;
    wherein said at least one substance capable of increasing firmness of the firm particles is selected from the group consisting of calcium salts, potassium salts, monohydric $C_1$- to $C_5$-alcohols and polyhydric $C_1$- to $C_5$-alcohols;
    wherein said firm and shape-retaining gel contains from 0.2 to 1 wt. % of said calcium and/or potassium salts when said salts are present and contains at least 15 wt. % of said monohydric and/or polyhydric alcohols when said alcohols are present;
    wherein said fluid phase contains at least one fluid ingredient selected from the group consisting of alkylene glycols with $C_2$- to $C_5$-alkylene groups, glycerol, liquid polyalkylene glycols, polyethylene glycol $C_1$- to $C_4$-alkyl ethers, polypropylene glycol $C_1$- to $C_4$-alkyl ethers, ethylene glycol-propylene glycol copolymers and polyoxyethylene-polyoxypropylene $C_1$- to $C_4$-alkyl ethers; and
    wherein said two-phase gel is made by a method comprising preparing the firm and shape-retaining gel, comminuting the firm and shape-retaining gel to form the firm particles, and then adding the fluid phase to the firm particles.

2. The agent as defined in claim 1, wherein said firm particles have a resistance to compression under standard conditions (20° C., 65% relative humidity) amounting to at least 0.15 N, as measured by penetration of the firm and shape-retaining gel with a cylindrical plunger having a diameter of 8 mm, the penetration being carried out at a rate of 0.5 mm/sec to a compression depth of 1 mm, after which the plunger is withdrawn at a rate of 0.5 mm/sec.

3. The agent as defined in claim 1, wherein the at least one fluid ingredient is selected from the group consisting of alkylene glycols with $C_2$- to $C_5$-alkylene groups, glycerol and liquid polyalkylene glycols.

4. The agent as defined in claim 1, wherein said carrageenan is kappa-carrageenan or a carrageenan mixture containing said kappa-carrageenan.

5. The agent as defined in claim 1, wherein said at least one hair-firming polymer is selected from the group consisting of anionic hair-firming polymers, nonionic hair-firming polymers and amphoteric hair-firming polymers.

6. The agent as defined in claim 1, further comprising at least one substance capable of facilitating spreadability on hair, said at least one substance being selected from the group consisting of amphiphilic associative thickeners, xanthan gum and cellulose derivatives.

7. The agent as defined in claim 1, further comprising at least one sugar.

8. The agent as defined in claim 7, wherein said at least one sugar is selected from the group consisting of glucose, galactose, fructose, maltose, lactose and sucrose.

9. The agent as defined in claim 1, containing from 30 to 95 wt. % of said firm particles and from 5 to 70 wt. % of said fluid matrix.

10. The agent as defined in claim 1, further comprising at least one propellant.

11. The agent as defined in claim 10, wherein said at least one propellant is dimethyl ether.

12. A hair-treatment product consisting of (a) a pressure-resistant container; (b) a propellant-containing hair-treatment agent as defined in claim 1 contained in said pressure-resistant container; and (c) a device for spraying or foaming the hair-treatment agent contained in said pressure-resistant container.

* * * * *